US009449385B2

(12) United States Patent
Petschke et al.

(10) Patent No.: US 9,449,385 B2
(45) Date of Patent: Sep. 20, 2016

(54) RECONSTRUCTION OF COMPUTED TOMOGRAPHY IMAGES USING COMBINED THIRD-GENERATION AND FOURTH-GENERATION PROJECTION DATA

(71) Applicant: Toshiba Medical Systems Corporation, Otawara-shi (JP)

(72) Inventors: Adam Petschke, Lake Bluff, IL (US); Yu Zou, Naperville, IL (US); Zhou Yu, Palatine, IL (US)

(73) Assignee: Toshiba Medical Systems Corporation, Otawara-shi (JP)

( * ) Notice: Subject to any disclaimer, the term of this patent is extended or adjusted under 35 U.S.C. 154(b) by 31 days.

(21) Appl. No.: 14/293,427

(22) Filed: Jun. 2, 2014

(65) Prior Publication Data

US 2015/0348258 A1  Dec. 3, 2015

(51) Int. Cl.
*G06T 7/00* (2006.01)
*A61B 6/03* (2006.01)
*A61B 6/00* (2006.01)
*G06T 5/00* (2006.01)
*G06T 11/00* (2006.01)

(52) U.S. Cl.
CPC ............ *G06T 7/0012* (2013.01); *A61B 6/032* (2013.01); *A61B 6/4241* (2013.01); *A61B 6/4266* (2013.01); *A61B 6/4275* (2013.01); *A61B 6/4441* (2013.01); *A61B 6/482* (2013.01); *A61B 6/5205* (2013.01); *A61B 6/5217* (2013.01); *A61B 6/5235* (2013.01); *A61B 6/5258* (2013.01); *G06T 5/001* (2013.01); *G06T 11/003* (2013.01); *G06T 11/008* (2013.01); *G06T 2207/10072* (2013.01); *G06T 2211/408* (2013.01)

(58) Field of Classification Search
CPC .... A61B 6/032; A61B 6/4241; A61B 6/482; A61B 6/5205; A61B 6/4266; A61B 6/4275; A61B 6/4441; A61B 6/5217; A61B 6/5235; A61B 6/5258; G06T 2207/10072; G06T 5/001; G06T 7/0012; G06T 11/003; G06T 11/008; G06T 2211/408
USPC .................................................. 382/128, 131
See application file for complete search history.

(56) References Cited

U.S. PATENT DOCUMENTS

2013/0343517 A1* 12/2013 Gagnon .................... G01T 1/24
378/19
2014/0355853 A1    12/2014 Zou et al.
2015/0043796 A1*  2/2015 Rigie ................... G06T 11/005
382/131

(Continued)

FOREIGN PATENT DOCUMENTS

JP     2007-167663 A     7/2007

*Primary Examiner* — Tom Y Lu
(74) *Attorney, Agent, or Firm* — Oblon, McClelland, Maier & Neustadt, L.L.P.

(57) ABSTRACT

An apparatus is provided to reconstruct an image using combined third-generation energy-integrating computed tomography projection data and fourth-generation spectrally resolved computed tomography projection data. The apparatus includes processing circuitry configured to obtain first projection data representing projection data from an energy-integrating detector; obtain second projection data representing projection data from a photon-counting spectrally discriminating detector; and reconstruct a first combined-system basis image and a second combined-system basis image by solving a combined-system matrix equation using the first projection data and the second projection data.

20 Claims, 7 Drawing Sheets

(56) References Cited

U.S. PATENT DOCUMENTS

| | | | |
|---|---|---|---|
| 2015/0146844 A1* | 5/2015 | Zamyatin | A61B 6/032 378/5 |
| 2015/0178957 A1* | 6/2015 | Zou | G06T 11/005 382/131 |
| 2015/0238157 A1* | 8/2015 | Shi | A61B 6/5205 378/4 |

* cited by examiner

RECONSTRUCTION OF COMPUTED TOMOGRAPHY IMAGES USING COMBINED THIRD-GENERATION AND FOURTH-GENERATION PROJECTION DATA

FIELD

Embodiments described herein relate generally to a method of reconstructing computed tomography images, and more specifically to reconstructing computed tomography images using combined third-generation and fourth-generation computed tomography data.

BACKGROUND

The X-ray beam in most computer tomography (CT) scanners is generally polychromatic. Yet, third-generation CT scanners generate images based upon data according to the energy integration nature of the detectors. These conventional detectors are called energy-integrating detectors and acquire energy integration X-ray data. On the other hand, photon-counting detectors are configured to acquire the spectral nature of the X-ray source, rather than the energy integration nature. To obtain the spectral nature of the transmitted X-ray data, the photon-counting detectors split the X-ray beam into its component energies or spectrum bins and count a number of photons in each of the bins. The use of the spectral nature of the X-ray source in CT is often referred to as spectral CT. Since spectral CT involves the detection of transmitted X-ray at two or more energy levels, spectral CT generally includes dual-energy CT by definition.

Spectral CT is advantageous over conventional CT. Spectral CT offers the additional clinical information inherent in the full spectrum of an X-ray beam. For example, spectral CT facilitates in discriminating tissues, differentiating between materials such as tissues containing calcium and iodine, and enhancing the detection of smaller vessels. Among other advantages, spectral CT is also expected to reduce beam-hardening artifacts. Spectral CT is also expected to increase accuracy in CT numbers independent of scanners.

Conventional attempts included the use of the integrating detectors in implementing spectral CT. One attempt included dual sources and dual integrating detector units that are placed on the gantry at a predetermined angle with each other for acquiring data as the gantry rotates around a patient. Another attempt included a single source that performs kV-switching and a single integrating detector unit that are placed on the gantry for acquiring data as the gantry rotates around a patient. Yet another attempt included a single source and dual integrating detector units that are layered on the gantry for acquiring the data as the gantry rotates around a patient. All of these attempts at spectral CT were not successful in substantially solving issues such as beam hardening, temporal resolution, noise, poor detector response, poor energy separation, etc. for reconstructing clinically viable images.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION

Figure 1:
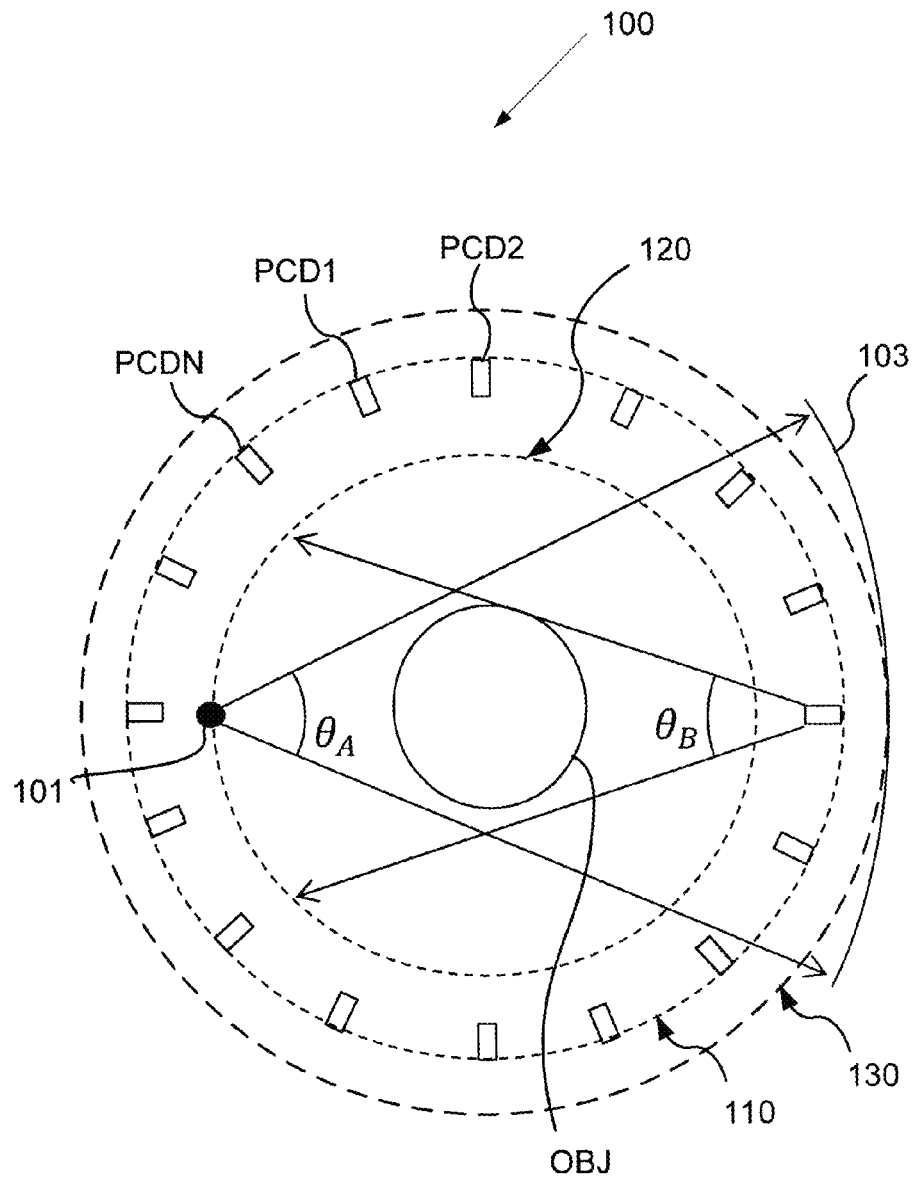
FIG. 1 shows a diagram of a cross-section of a combined third-generation and fourth generation computed tomography apparatus.

Combined third-generation and fourth-generation CT systems use arrays of sparsely spaced fourth-generation photon-counting detectors and more densely packed arrays of third-generation energy integrating detectors. However, for combined third-generation and fourth-generation CT systems, there has been no analytical solution for image reconstruction.

In one embodiment, there is provided an apparatus to reconstruct an image using combined third-generation energy-integrating computed tomography projection data and fourth-generation spectrally resolved computed tomography projection data, the apparatus comprising: processing circuitry configured to (1) obtain first projection data from an energy-integrating detector; (2) obtain second projection data from a photon-counting spectrally discriminating detector; and (3) reconstruct a first combined-system basis image and a second combined-system basis image by solving a combined-system matrix equation using the first projection data and the second projection data.

In another embodiment, the processing circuitry is further configured to: (1) calculate a first basis image of a first material using the second projection data; (2) calculate a second basis image of a second material using the second projection data; and (3) correct the first projection data to remove effects of beam hardening by calculating a beam-hardening correction using the first basis image and the second basis image.

In another embodiment, the processing circuitry is further configured to solve the combined-system matrix equation by an iterative computed tomography image reconstruction method.

In another embodiment, the processing circuitry is further configured to solve the combined-system matrix equation by calculating a pseudoinverse matrix of a combined-system matrix.

In another embodiment, there is provided a computed tomography apparatus, comprising: (1) a polychromatic X-ray source; (2) an energy-integrating X-ray detector configured to generate first projection data; (3) a photon-counting X-ray detector configured to generate second projection data; and (4) processing circuitry configured to reconstruct a first combined-system basis image and a second combined-system basis image by solving a combined-system matrix equation using the first projection data and the second projection data.

In another embodiment, there is provided a method of image reconstruction using combined third-generation energy-integrating computed tomography projection data and fourth-generation spectrally resolved computed tomography projection data, the method comprising: (1) obtaining first projection data from an energy-integrating detector; (2) obtaining second projection data from a photon-counting spectrum-resolving detector; and (3) reconstructing a first combined-system basis image and a second combined-system basis image by solving a combined-system matrix equation using the first projection data and the second projection data.

In another embodiment, the method further comprises respectively setting the first basis image and the second basis image equal to the corresponding first combined-system basis image and second combined-system basis image; correcting the first projection data to remove the effects of beam hardening by calculating another beam-hardening correction using the first basis image and the second basis image; and reconstructing another first combined-system basis image and another second combined-system basis image by solving the combined-system matrix equation using the corrected first projection data and the second projection data.

Referring now to the drawings, wherein like reference numerals designate identical or corresponding parts throughout the several views, FIG. 1 shows a diagram illustrating an implementation for placing the photon-counting detectors (PCDs) in a predetermined fourth-generation geometry in combination with a detector unit in a predetermined third-generation geometry in a CT scanner system. The diagram illustrates relative positions among an object OBJ to be scanned, an X-ray source 101, an X-ray detector 103, and the photon-counting detectors PCD1 through PCDN in one exemplary embodiment. For the sake of simplicity, the diagram excludes other components and units that are necessary in acquiring and processing data as well as reconstructing an image based upon the acquired data. In general, the photon-counting detectors PCD1 through PCDN each output a photon count for each predetermined energy bin. In addition to the sparse photon-counting detectors PCD1 through PCDN in the fourth-generation geometry, the implementation shown in FIG. 1 includes a detector unit such as the detector 103 in a conventional third-generation geometry in the CT scanner system. The detector elements in the detector unit 103 can be more densely placed along the detector unit surface than the photon-counting detectors.

In one implementation, the photon-counting detectors are sparsely placed around the object OBJ in a predetermined geometry such as a circle. For example, the photon-counting detectors PCD1 through PCDN are fixedly placed on a predetermined circular component 110 in the gantry 100. In one implementation, the photon-counting detectors PCD1 through PCDN are fixedly placed on the circular component 110 at predetermined equidistant positions. In an alternative implementation, the photon-counting detectors PCD1 through PCDN are fixedly placed on the circular component 110 at predetermined non-equidistant positions. The circular component 110 remains stationary with respect to the object OBJ and does not rotate during the data acquisition.

Both the X-ray source 101 and the detector unit 103 rotate around the object OBJ while the photon-counting detectors PCD1 through PCDN are stationary with respect to the object OBJ. In one implementation, the X-ray source 101 is mounted on a first rotating portion 120 such as the annular frame in the gantry 100 so that the X-ray source 101 projects X-ray radiation with a predetermined source fan beam angle $\theta_A$ towards the object OBJ while the X-ray source 101 rotates around the object OBJ inside the sparsely placed photon-counting detectors PCD1 through PCDN. Furthermore, an additional detector unit 103 is mounted on a second rotating portion 130 in the third-generation geometry. The rotating portion 130 mounts the detector unit 103 at a diametrically opposed position from the X-ray source 101 across the object OBJ and rotates outside the stationary circular component 110, on which the photon-counting detectors PCD1 through PCDN are fixedly placed in a predetermined sparse manner.

In one implementation, the rotating portions 120 and 130 are integrally constructed as a single component, such as the annular frame 102, to maintain a 180-degree angle between the X-ray source 101 and the detector unit 103 as they rotate about the object OBJ with a different radius. In an optional implementation, the rotating portions 120 and 130 are separate components, but synchronously rotate to maintain the X-ray source 101 and the detector unit 103 in the fixedly opposed positions at 180 degrees across the object OBJ. Furthermore, the X-ray source 101 optionally travels a helical path as the object is moved in a predetermined direction that is perpendicular to the rotational plane of the rotating portion 120.

As the X-ray source 101 and the detector unit 103 rotate around the object OBJ, the photon-counting detectors PCDs and the detector unit 103 respectively detect the transmitted X-ray radiation during data acquisition. The photon-counting detectors PCD1 through PCDN intermittently detect with a predetermined detector fan beam angle $\theta_B$ the X-ray radiation that has been transmitted through the object OBJ and individually output a count value representing a number of photons, for each of predetermined energy bins. On the other hand, the detector elements in the detector unit 103 continuously detect the X-ray radiation that has been transmitted through the object OBJ and output the detected signals as the detector unit 103 rotates. In one implementation, the detector unit 103 has densely placed energy-integrating detectors in predetermined channel and segment directions on the detector unit surface.

In one implementation, the X-ray source 101, the photon-counting detectors and the detector unit 103 collectively form three predetermined circular paths that differ in radius. The photon-counting detectors are sparsely placed along a first circular path around the object OBJ while at least one X-ray source 101 rotates along a second circular path around the object OBI Further, the detector unit 103 travels along a third circular path. The above exemplary embodiment illustrates that the third circular path is the largest and outside the first and second circular paths around the object OBJ. Although not illustrated, an alternative embodiment optionally changes the relative relation of the first and second circular paths so that the second circular path for the X-ray source 101 is larger and outside the first circular path of the sparsely placed photon-counting detectors PCD1 through PCDN around the object OBJ. Furthermore, in another alternative embodiment, the X-ray source 101 also optionally travels on the same third circular path as the detector unit 103. Furthermore, the above alternative embodiments optionally provide a protective rear cover for each of the photon-counting detectors that are irradiated from behind in a short distance as the X-ray source 101 travels outside the first circular path of the sparsely placed photon-counting detectors.

There are other alternative embodiments for placing the photon-counting detectors in a predetermined fourth-generation geometry in combination with the detector unit in a predetermined third-generation geometry in the CT scanner.

The X-ray source 101 is optionally a single energy source in certain embodiments. By the same token, an additional alternative embodiment optionally includes the X-ray source 101, which is configured to perform a kV-switching function for emitting X-ray radiation at a predetermined high-level energy and at a predetermined low-level energy.

In general, the photon-counting detectors PCD1 through PCDN are sparsely positioned along the circular component 110. Although the photon-counting detectors PCD1 through PCDN acquire sparse view projection data, the acquired projection data is sufficient for at least dual-energy (DE) reconstruction with a sparse view reconstruction technique. In addition, the detector unit 103 also acquires another set of projection data, and the projection data from the detector unit 103 is used to generally improve image quality. In case that the detector unit 103 consists of energy-integrating detectors with anti-scatter grids, the projection data from the detector unit 103 is used to correct scatter on the projection data from the photon-counting detectors. In one implementation, the integrating detectors optionally need to be calibrated in view of X-ray transmission through the predetermined circular component 110 and some of the photon-counting detectors. In acquiring the projection data, a sampling on the source trajectory is optionally made dense in order to enhance spatial resolution.

Figure 2:
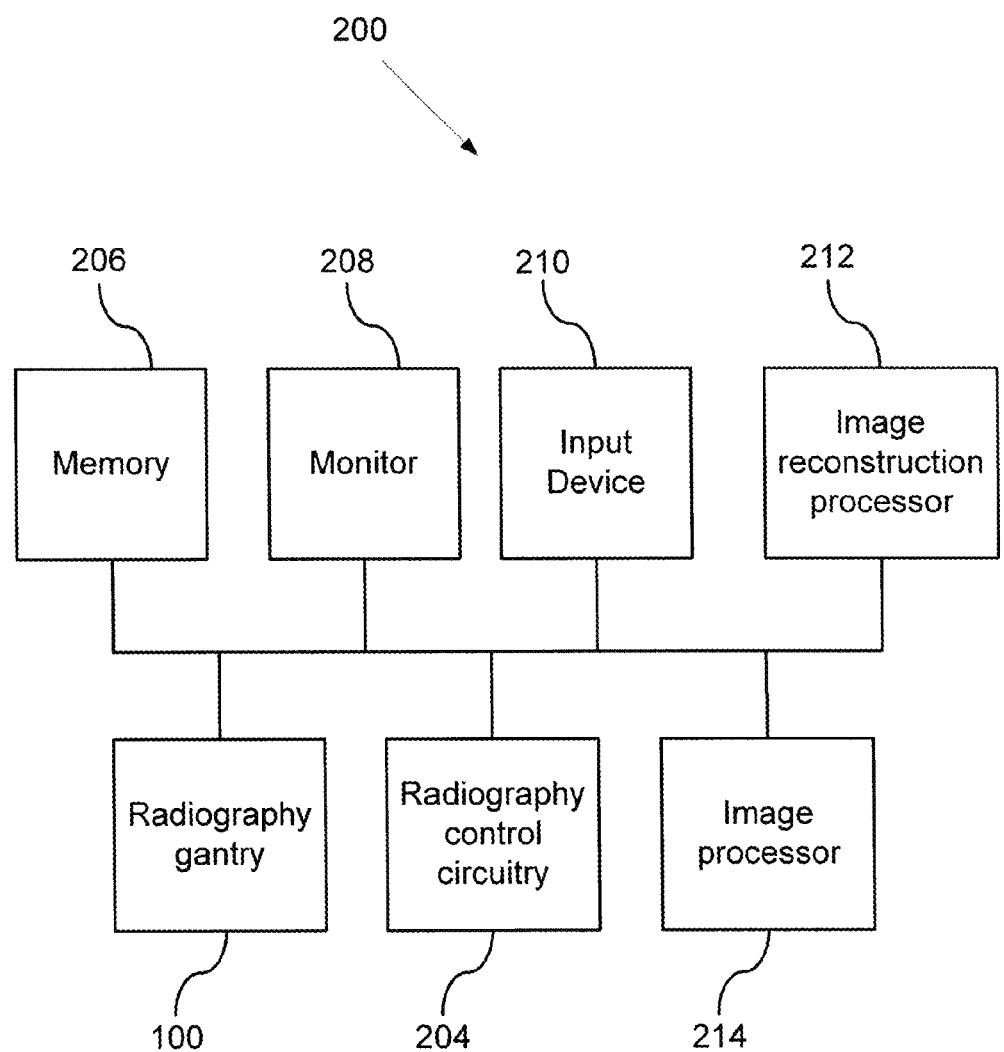
FIG. 2 shows a schematic of a computed tomography system.

FIG. 2 shows a schematic of an X-ray CT scanner system 200. The X-ray CT scanner system 200 comprises a radiography gantry 100, radiography control circuitry 204, memory 206, monitor 208, input device 210, image reconstruction unit 212, and image processor 214.

Figure 3:
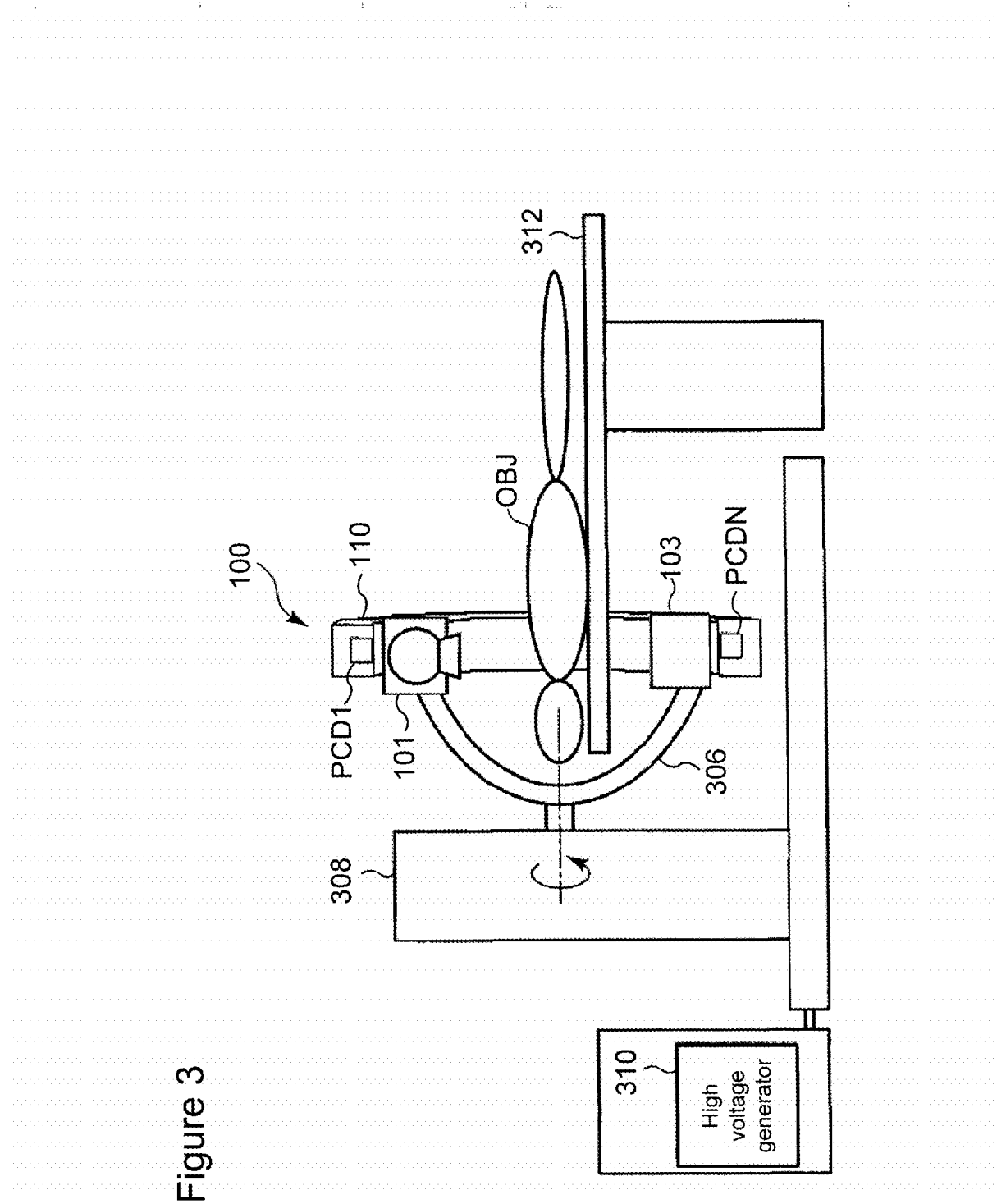
FIG. 3 shows an implementation of a computed tomography system.

FIG. 3 shows an example of the outer appearance of the radiography gantry 100. As shown in FIG. 3, the radiography gantry 2 includes an X-ray source 101, a third-generation energy-integrating X-ray detector 103, a plurality of fourth-generation photon-counting detectors PCD1 through PCDN arranged on a stationary circular component 110, a C-arm 306, a stand 308, a high voltage generator 310, and a bed 312.

The high voltage generator 310 generates a high voltage to be applied between the electrodes of the X-ray source 101. Upon receiving the high voltage and filament current, the X-ray source 101 generates X-ray radiation. The third-generation X-ray detector 103 is a two-dimensional array of energy integrating detection elements (pixels) which directly or indirectly convert incident X-ray radiation into electric charges. The photon-counting detectors in a fourth-generation geometry are sparsely arranged along the stationary circular component 110. In FIG. 3 the stationary circular component 110 is shown to be semicircular in shape. In an alternative implementation, the shape of the stationary circular component 110 can be a complete circle. The X-ray source 101 is mounted on, for example, one end of the floor type C-arm 306. The third-generation X-ray detector 103 is mounted on the other end of the C-arm 306. The third-generation X-ray detector 103 faces the X-ray source 101 through an object OBJ to be examined which is placed on the bed 312. The C-arm 306 is rotatably supported on the stand 308. Repeating radiography with respect to the object OBJ while rotating the C-arm 306 makes it possible to acquire X-ray images (projection data) in many directions which are required for CT image reconstruction.

In an alternative implementation, rather than being mounted to a C-arm 306, the X-ray source 101, third-generation X-ray detector 103, and fourth-generation photon-counting X-ray detectors can be mounted to annular frames that completely encircle the object OBJ. As shown in FIG. 1, the third-generation energy integrating detectors can be arranged in a predetermined third-generation geometry, and the photon-counting detectors can be arranged in a predetermined fourth-generation geometry. The annular frame can be fixed in space and the X-ray source 101 moves relative to the annular frame, as shown in FIG. 1. Also, the energy-integrating detectors in the predetermined third-generation geometry can also move relative to the annular frame, as shown in FIG. 1.

The radiography control circuitry 204 controls the rotation of the C-arm 306, the application of high voltages from the high voltage generator 310 to the X-ray source 101, and the reading of signals from the X-ray detector 304 in order to execute rotational radiography and generate X-ray projection data.

The memory 206 stores a dedicated program for executing a combined third-generation and fourth-generation image reconstruction method to be described below.

The monitor 208 is a display device such as a CRT, plasma display, or liquid crystal display which displays an X-ray diagnostic image in a predetermined form in accordance with a signal received from the image reconstruction processor 212 or the image processor 214.

The input device 210 includes a keyboard, various kinds of switches, a mouse, etc. and is used to input a radiography instruction, image selection instruction, etc. The image reconstruction processor 212 reconstructs volume data from projection images in a plurality of projection directions.

The image processor 214 executes predetermined image processing such as volume rendering processing and image difference processing as needed.

Figure 4:
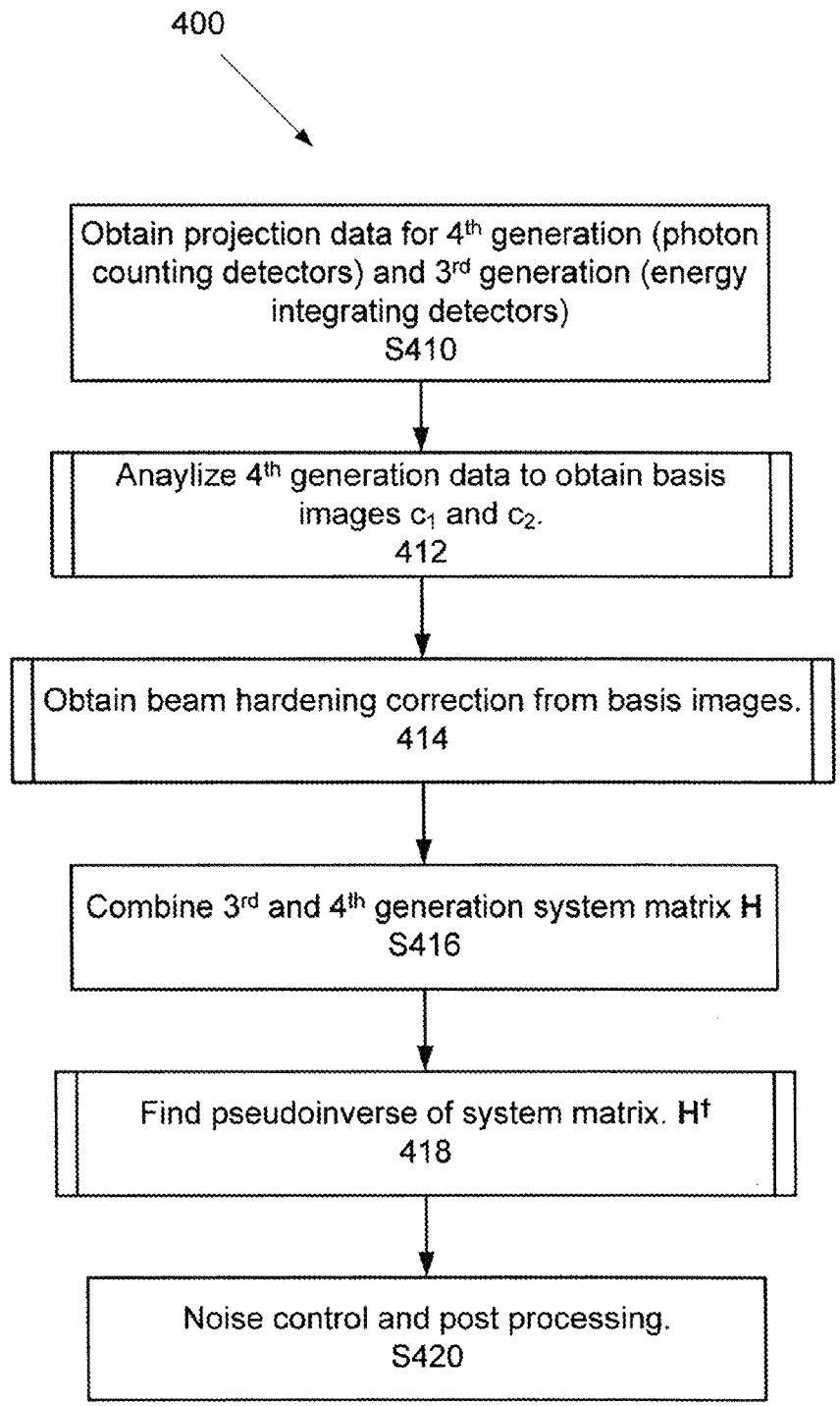
FIG. 4 shows a flow diagram of a method to reconstruct a combined image from combined third-generation and fourth generation computed tomography projection data.

FIG. 4 shows a method 400 for reconstructing a tomographic image of an object OBJ from a series of projections through the object OBJ using a combined third-generation and fourth-generation CT scanner system.

The first step S410 of the combined third-generation and fourth-generation image reconstruction method 400 is to obtain the projection data at multiple projection directions.

Figure 5:
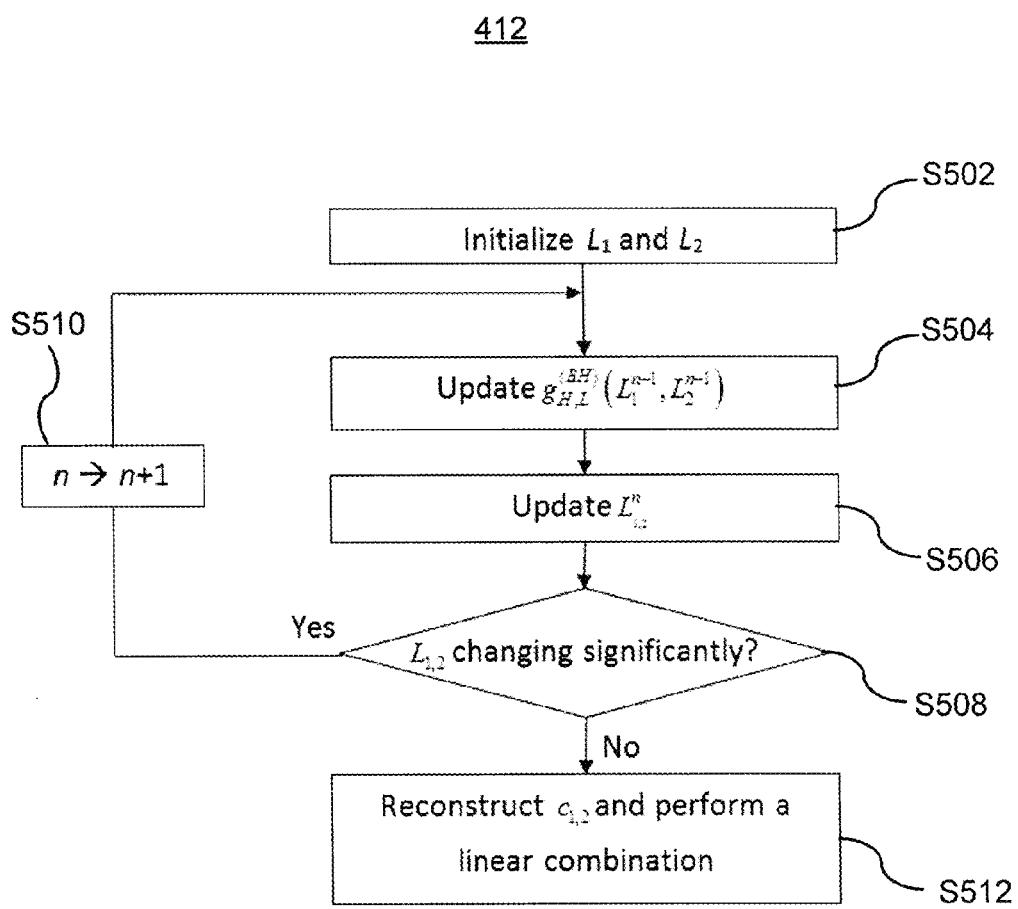
FIG. 5 shows a flow diagram of a method for reconstructing two basis images for dual-energy computed tomography.

The second step of method 400 is performing process 412 to reconstruct two basis images, i.e., $c_1$ and $c_2$. FIG. 5 shows an implementation of process 412 where a dual-energy analysis method is used to find the basis images $c_1$ and $c_2$.

A dual-energy analysis method can be used because the attenuation of X-rays in biological materials is dominated by two physical processes (i.e., photoelectric scattering and Compton scattering). Thus, the attenuation coefficient as a function of energy can be approximated by the decomposition $$\mu(E,x,y) = \mu_{PE}(E,x,y) + \mu_C(E,x,y),$$

where $\mu_{PE}(E,x,y)$ is the photoelectric attenuation and $\mu_C(E,x,y)$ is the Compton attenuation. This attenuation coefficient can be rearranged instead into a decomposition of a high-Z material (i.e., material 1) and a low-Z material (i.e., material 2) to become $$\mu(E,x,y) \approx \mu_1(E)c_1(x,y) + \mu_2(E)c_2(x,y).$$

By iteratively performing process 412, the polychromatic projection data from the fourth-generation photon-counting detectors can be decomposed into two material components (e.g., a high-Z material component and a low-Z material component), and using known CT reconstruction method, these two projection data components are used to reconstruct the two basis images $c_1(x,y)$ and $c_2(x,y)$ corresponding respectively to material 1 and material 2. For better results using process 412, most of the X-ray energy should be below the K-edge of the predominant materials in object OBJ, which is easily satisfied for biological materials and standard X-ray sources.

For the high and low X-ray energies, the detected intensities are respectively $$I_H(l) = \int S_H(E) \exp[-\mu_1(E)\int_l c_1(x,y)dl - \mu_2(E)\int_l c_2(x,y)dl]dE$$

$$I_L(l) = \int S_L(E) \exp[-\mu_1(E)\int_l c_1(x,y)dl - \mu_2(E)\int_l c_2(x,y)dl]dE$$

where $S_H(E)$ and $S_L(E)$ are respectively the detected high- and low-energy spectra in the absence of the object OBJ, and where $S_H(E)$ and $S_L(E)$ have been normalized such that $$\int dE S_H(E) = \int dE S_L(E) = 1.$$

The terms $S_H(E)$ and $S_L$ include loses due to transmission through various X-ray elements (e.g., a bowtie filter at the source and spectral filters at the detectors) and system efficiencies (e.g., the quantum efficiency of the X-ray detectors $\eta_{H,L}(E)$).

There are numerous dual-energy configurations for obtaining high- and low-energy spectra. In one implementation, $S_H(E)$ and $S_L(E)$ result from different X-ray source spectra (e.g., using two sources with different energy spectra, or a single source using kV-switching). In another implementation, a single multispectral beam $S_0(E)$ is incident on the object OBJ and after passing through the object OBJ the X-rays are resolved into spectral components (e.g., by spectral filters placed in front of energy-integrating detectors or by photon-counting detectors). In the case of a single incident beam the high- and low-energy spectra are respectively given by $$S_H(E) = \bar{R}_1^{(H)}(E)S_0(E), \text{ and } S_L(E) = \bar{R}_1^{(L)}(E)S_0(E),$$

where $\bar{R}_1^{(H,L)}(E)$ is a linear detector response term that acts as a spectral filter on the incident beam $S_0(E)$. In one implementation, $\bar{R}_1^{(H,L)}(E)$ can be determined using the method of noise balancing as discussed in U.S. patent application Ser. No. 13/906,110, incorporated herein by reference in its entirety.

In certain implementations, different rays within an X-ray cone beam can have different spectra. When the energy spectra depend on the direction of the ray, the energy spectra can respectively be written as $S_H(E,l)$ and $S_L(E,l)$ to include a dependency on the ray trajectory $l$.

By taking the natural logarithm of the intensity, the projection data are obtained as $$g_H(l) = -\ln \int S_H(E) \exp[-\mu_1(E)L_1(l) - \mu_2(E)L_2(l)]dE$$

$$g_L(l) = -\ln \int S_L(E) \exp[-\mu_1(E)L_1(l) - \mu_2(E)L_2(l)]dE$$

where $L_{1,2}(l) = \int_l c_{1,2}(x,y) \, dl$ is the Radon transform for a ray of the X-ray beam along the trajectory/path $l$.

After solving the dual-energy problem to obtain the two material projection values $L_1$ and $L_2$, the solutions $L_1$ and $L_2$ can be processed using known CT reconstruction methods to obtain the basis images $c_1(x,y)$ and $c_2(x,y)$.

In one implementation, as shown in FIG. 5, $L_1$ and $L_2$ are found using perturbation theory by treating the variations around the mean of the attenuation coefficients $\mu_1(E)$ and $\mu_2(E)$ as perturbations. First, the mean attenuation for the high- and low-energy spectra are given by $$\bar{\mu}_{1,2}^{H,L} = \int S_{H,L}(E)\mu_{1,2}(E)dE$$

and the variations around the mean are given as a function of the X-ray energy to be $$\Delta\mu_{1,2}^{H,L}(E) = \mu_{1,2}(E) - \bar{\mu}_{1,2}^{H,L}.$$

Thus, the projection data can be expressed as $$g_H(l) = -\ln \int S_H(E) \exp[-\bar{\mu}_1^H L_1(l) - \Delta\mu_1^H(E)L_1(l) - \bar{\mu}_2^H L_2(l) - \Delta\mu_2^H(E)L_2(l)]dE$$

$$g_L(l) = -\ln \int S_L(E) \exp[-\bar{\mu}_1^L L_1(l) - \Delta\mu_1^L(E)L_1(l) - \bar{\mu}_2^L L_2(l) - \Delta\mu_2^L(E)L_2(l)]dE.$$

The projection data then simplify to $$g_H(l) = \bar{\mu}_1^H L_1(l) + \bar{\mu}_2^H L_2(l) - g_H^{(BH)}(L_1(l), L_2(l))$$

$$g_L(l) = \bar{\mu}_1^L L_1(l) + \bar{\mu}_2^L L_2(l) - g_L^{(BH)}(L_1(l), L_2(l))$$

where $$g_{H,L}^{(BH)}(L_1(l), L_2(l)) = \ln \int S_{H,L}(E) \exp[-L_1(l)\Delta\mu_1^{H,L}(E) - L_2(l)\Delta\mu_2^{H,L}(E)]dE$$

is the beam-hardening perturbation.

The first step S502 of process 412 is initializing n=0 and also initializing the values $L_1$ and $L_2$ to their respective the zeroth order perturbation values by solving the matrix equation $$\begin{pmatrix} g_H \\ g_L \end{pmatrix} = \begin{pmatrix} \bar{\mu}_1^H & \bar{\mu}_2^H \\ \bar{\mu}_1^L & \bar{\mu}_2^L \end{pmatrix} \begin{pmatrix} L_1 \\ L_2 \end{pmatrix}$$

to obtain $$\begin{pmatrix} L_1 \\ L_2 \end{pmatrix} = D^{-1} \begin{pmatrix} \bar{\mu}_2^L & \bar{\mu}_2^H \\ \bar{\mu}_1^L & \bar{\mu}_1^H \end{pmatrix} \begin{pmatrix} g_H \\ g_L \end{pmatrix}$$

where D is the determinant $D = \bar{\mu}_1^H \bar{\mu}_2^L - \bar{\mu}_1^L \bar{\mu}_2^H$.

The second step S504 of process 412 is to update the beam-hardening perturbation values using the nth order perturbation in the equation $$g_{H,L}^{(BH)}(L_1(l), L_2(l)) = \ln \int S_{H,L}(E) \exp[-L_1(l)\Delta\mu_1^{H,L}(E) - L_2(l)\Delta\mu_2^{H,L}(E)]dE.$$

The third step S506 of process 412 is to update the values of $L_1$ and $L_2$ by solving for the n+1th perturbation by solving the matrix equation $$\begin{pmatrix} g_H - g_H^{(BH)}(L_1, L_2) \\ g_L - g_L^{(BH)}(L_1, L_2) \end{pmatrix} = \begin{pmatrix} \bar{\mu}_1^H & \bar{\mu}_2^H \\ \bar{\mu}_1^L & \bar{\mu}_2^L \end{pmatrix} \begin{pmatrix} L_1 \\ L_2 \end{pmatrix}$$

to obtain $$\begin{pmatrix} L_1^n \\ L_2^n \end{pmatrix} = D^{-1} \begin{pmatrix} \bar{\mu}_2^L & -\bar{\mu}_2^H \\ -\bar{\mu}_1^L & \bar{\mu}_1^H \end{pmatrix} \begin{pmatrix} g_H - g_H^{(BH)}(L_1^{n-1}, L_2^{n-1}) \\ g_L - g_L^{(BH)}(L_1^{n-1}, L_2^{n-1}) \end{pmatrix}.$$

Next, step S508 of process 412 inquiries whether the values $L_1$ and $L_2$ have adequately converged according to some predetermined criteria, such as whether the difference between each current value of $L_1$ and $L_2$ and each corresponding previous value of $L_1$ and $L_2$ are less than a predetermined fraction of each current value of $L_1$ and $L_2$. If $L_1$ and $L_2$ have not adequately converged, the perturbation index is incremented and the loop repeats starting at step S504. Otherwise, process 412 proceeds to step S512.

In step S512 of process 412, the basis images $c_1(x,y)$ and $c_2(x,y)$ are obtained by solving the image reconstruction problem using known CT reconstruction techniques, such as the filtered backprojection (FBP) method, the true cone-beam tomography (TOCT) method, an iterative reconstruction method such as Kacmarz's method, or a statistical method such as the expectation maximization method. The image reconstruction can be formulated as a matrix equation problem by arranging the values $L_1(l)$ and $L_2(l)$ for each ray trajectory l as the column values of vectors $\vec{L}_1$ and $\vec{L}_2$ respectively. Similarly, the basis images $c_1(x,y)$ and $c_2(x,y)$ can also be arranged as column vectors $\vec{C}_1$ and $\vec{C}_2$ respectively. The image reconstruction problem can then be solved by solving the matrix equations $$A_{4th}\vec{C}_1 = \vec{L}_1, \text{ and } A_{4th}\vec{C}_2 = \vec{L}_2,$$

where $A_{4th}$ is the system matrix for the fourth-generation projection measurements (i.e., the Radon transform relating the image space of the object OBJ $\vec{C}_{1,2}$ to the projections $\vec{L}_{1,2}$). The column vectors $\vec{C}_1$ and $\vec{C}_2$ are related to the basis images by $$c_{1,2}(x, y) = \sum_n C_{1,2}[n] d_n(x, y),$$

where $$d_n(x, y) = \begin{cases} 1 & |x - x_n| < \epsilon \text{ and } |y - y_n| < \epsilon \\ 0 & \text{otherwise} \end{cases},$$

and $x_n$, and $y_n$ are respectively the x and y positions of the nth voxel of the object OBJ. The attenuation image is then given by $$\mu(E,x,y) = \mu_1(E) c_1(x,y) + \mu_2(E) c_2(x,y).$$

After reconstructing the basis images $c_1(x,y)$ and $c_2(x,y)$, the process 412 is complete and the method 400 proceeds to step 414.

Figure 6:
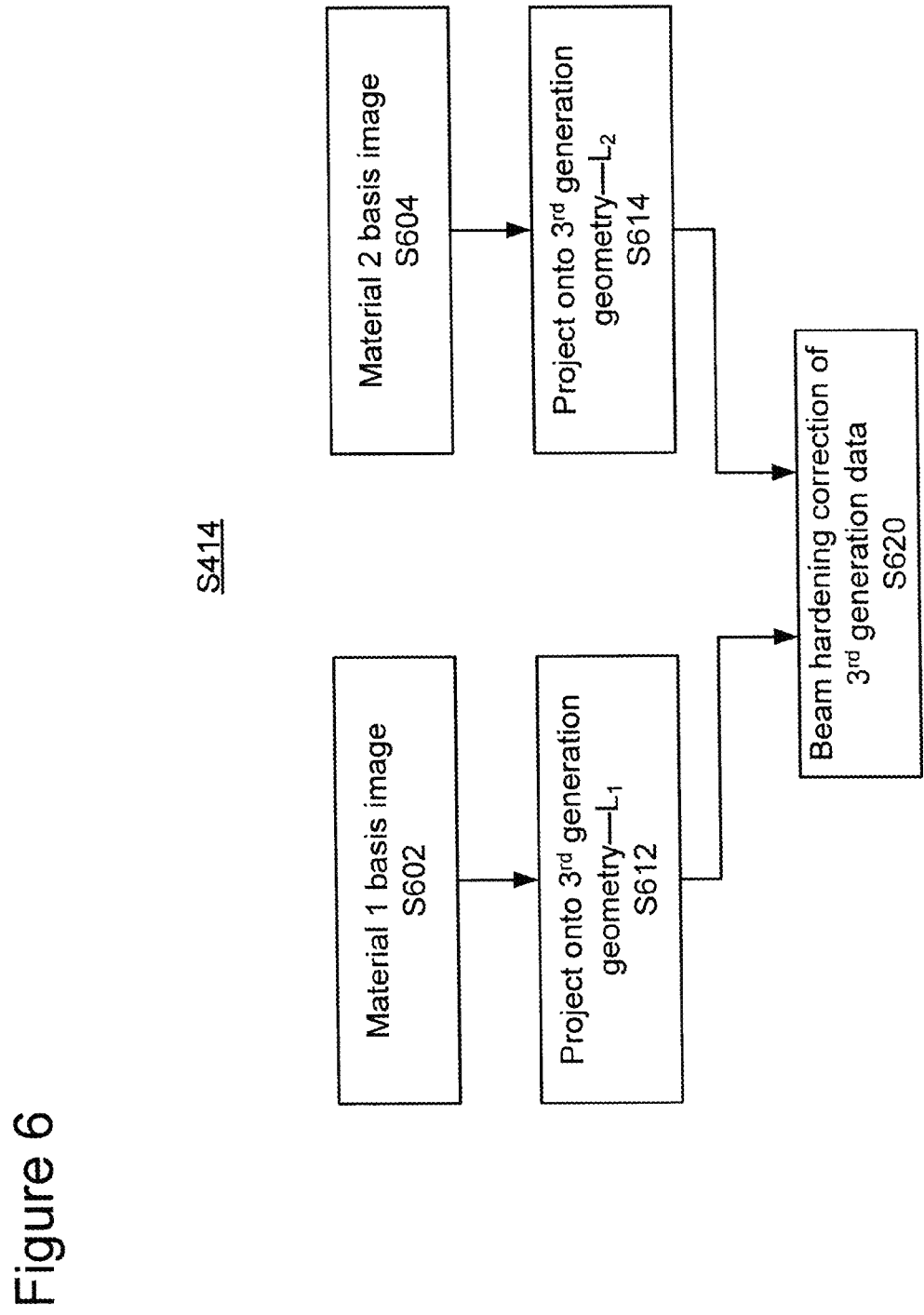
FIG. 6 shows a flow diagram of a method for combining two basis images to perform a beam-hardening correction of third-generation computed tomography projection data.

In FIG. 4, the third step 414 of method 400 is the process of correcting for the effects of beam hardening on the third-generation projection data. FIG. 6 shows an implementation of the beam-hardening correction process 414. The process 414 begins at steps S602 and S604 by obtaining the basis images as column vectors $\vec{C}_1$ and $\vec{C}_2$ resulting from the process 412. Next, at step S612 the material 1 basis images is projected onto the third-generation system matrix $A_{3rd}$ to obtain the value $$\vec{L}_1^{(3rd)} = A_{3rd}\vec{C}_1,$$

where each row vector of $A_{3rd}$ corresponds to the Radon transform of a respective ray trajectory l corresponding to each projection measurement $g_{3rd}(l)$ and l signifies the path of the line integral of the Radon transform. Similarly, at step S614 the material 2 basis image is projected onto the third-generation system matrix $A_{3rd}$ to obtain the value $$\vec{L}_2^{(3rd)} = A_{3rd}\vec{C}_2.$$

The beam-hardening correction for each value of the projection data is calculated as $$BHC(l) = \ln\int dES_{3rd}(E,l)\exp[-L_1^{(3rd)}(l)\Delta\mu_1^{(3rd)}(E,l) - L_2^{(3rd)}(l)\Delta\mu_2^{(3rd)}(E,l)],$$

where $$\Delta\mu_1^{3rd}(E,l) = \mu_1(E) - \int dES_{3rd}(E,l)\mu_1(E), \text{ and}$$

$$\Delta\mu_2^{3rd}(E,l) = 2(E) - \int dES_{3rd}(E,l)\mu_2(E).$$

The l in $S_{3rd}(E,l)$ reflects the fact that the energy spectra can be different for different ray trajectories in the X-ray beam. For example, in certain implementations, a bowtie filter having a spectrally varying absorption coefficient can be used between the X-ray source and the object OBJ. Because different ray trajectories pass through different thicknesses of the bowtie filter, each ray experiences a different amount of absorption. Rays transmitted through thinner portions of the bowtie filter experience less absorption and correspondingly smaller changes to their X-ray spectrum, while rays transmitted through thicker portions of the bowtie filter experience greater absorption and greater changes to their X-ray spectrum. Thus, even if all of the rays of the X-ray beam originated with identical spectra before the bowtie filter, after the bowtie filter, different rays will have different spectra. Each of the energy spectra discussed here is normalized such that $$\int dES_{3rd}(E) = 1,$$

$$\int dES_H(E) = 1, \text{ and}$$

$$\int dES_L(E) = 1.$$

The last step S620 of the beam-hardening correction process 414 calculates the third-generation projection data corrected for beam hardening given by $$g'_{3rd}(l) = g_{3rd}(l)/BHC(l).$$

After performing the beam-hardening correction, the method 400 proceeds to step S416, where the third-generation data and fourth-generation data are combined to form a single data set with an combined-system matrix H, where the combined-system matrix equation is given by $$\vec{g} = H\vec{f},$$

where $$\vec{g} = \begin{bmatrix} \vec{L}_1 \\ \vec{L}_2 \\ \vec{g}'_{3rd} \end{bmatrix},$$

$$H = \begin{bmatrix} A_{4th} & 0 \\ 0 & A_{4th} \\ M_1 A_{3rd} & M_2 A_{3rd} \end{bmatrix}, \text{ and}$$

$$\vec{f} = \begin{bmatrix} \vec{f}_1 \\ \vec{f}_2 \end{bmatrix}.$$

Next, the method 400 proceeds to process 418 to solve the combined-system matrix equation to reconstruct the combined image $\vec{f}$. There are many methods for solving the combined-system matrix equation $\vec{g} = H\vec{f}$. One method, shown in FIG. 4, is to calculate the pseudoinverse (sometimes called the Moore-Penrose pseudoinverse), which is given by $$H^\dagger = (H^* H)^{-1} H^*$$

where the superscript * signifies the Hermitian transpose and the superscript −1 stands for the matrix inverse. After solving for the pseudoinverse, the combined-system matrix equation can be solved by simple matrix multiplication:

$$\vec{f} = H^\dagger \vec{g}.$$

There are many alternative methods for calculating the pseudoinverse including using QR factorization or using the singular value decomposition (SVD). Given the SVD of H is H=UΣV*, the pseudoinverse of H is given by H$^{†}$=VΣ$^{-1}$U*. Because Σ is a diagonal matrix, the inverse is obtained by taking the reciprocal of each non-zero diagonal element. If the SVD is used for calculating the pseudoinverse matrix, one method of noise control and post processing in step S420 is to set small singular values along the diagonal of Σ to zero, where small singular values is defined by a predetermined criterion. For example, small singular values can be those singular values less than a predetermined fraction of the largest singular value times. Alternative, the small singular values can be those singular values less than the machine precision (e.g., the floating point precision if floating point numbers are used) of the image reconstruction processor 212 multiplied times a predetermined multiplicative factor. In addition to QR factorization and the singular value decomposition, other known methods for calculating the pseudoinverse of a matrix can be used.

In one implementation, a weighted pseudoinverse rather than the pseudoinverse, is used to solve the integrated system matrix equation. The weighted pseudoinverse can be calculated by $$H^w = (H^* K_f^{-1} H)^{-1} H^* K_f^{-1} = (K_f^{-1/2} H)^† K_f^{-1/2},$$

where $K_f$ is the covariance matrix of $\vec{f}$. Whereas using the pseudoinverse provides the least-square solution of the integrated system matrix equation, using the weighted pseudoinverse provides the maximum likelihood solution of the integrated system matrix equation.

In an alternative implementation, sparse matrix inversion techniques, such as Krylov subspace methods or iterative matrix inversion methods, such as the bi-conjugate gradient method and the generalized minimal residual method, can also be used to solve the combined-system matrix equation.

When the matrix H becomes so large that it becomes too computationally intensive to invert, the combined-system matrix equation can be solved using iterative reconstruction techniques such as Kaczmarz's method or the total value minimization method.

The last step S420 of method 400 is to perform noise control and other post processing steps. Noise control can be realized through various techniques, such as by preconditioning the matrix when applying the sparse matrix to solve the combined-system matrix equation, by setting the small singular values to zero when using the SVD pseudoinverse technique, or by choosing an appropriate regularization method when using an iterative reconstruction technique.

Additionally, various smoothing and image processing techniques can be applied in the post processing of the image in order to improve image quality or highlight relevant features of the image. For example, the final basis images $\vec{f}_1$ and $\vec{f}_2$ can be combined in various ways to map the attenuation, density, or effective Z of the object OBJ.

After completing step S420 of method 400, it may be desirable to further refine the basis images $\vec{f}_1$ and $\vec{f}_2$. This refinement can be achieved by setting the respective basis images $\vec{C}_1$ and $\vec{C}_2$ to be equally to the newly calculated values of the basis images $\vec{f}_1$ and $\vec{f}_2$, and repeating method 400 starting at step 414 obtain beam hardening correction from basis images $\vec{C}_1$ and $\vec{C}_2$. This process of feeding back the combined-system basis images $\vec{f}_1$ and $\vec{f}_2$ from step S420 to process 414 and repeating processes and steps 414, S416, 418, and S420 can be performed multiple times. In one implementation, the method 400 loops through the processes and steps 414, S416, 418, and S420 a predetermined number of time. In another implementation, the method 400 loops through the steps 414, S416, 418, and S420 repeatedly until the basis images $\vec{f}_1$ and $\vec{f}_2$ converge according to some predetermined convergence criteria (e.g., when the root mean square of the difference between the current and previous values of the basis images $\vec{f}_1$ and $\vec{f}_2$ is less than a predetermined threshold).

Figure 7:
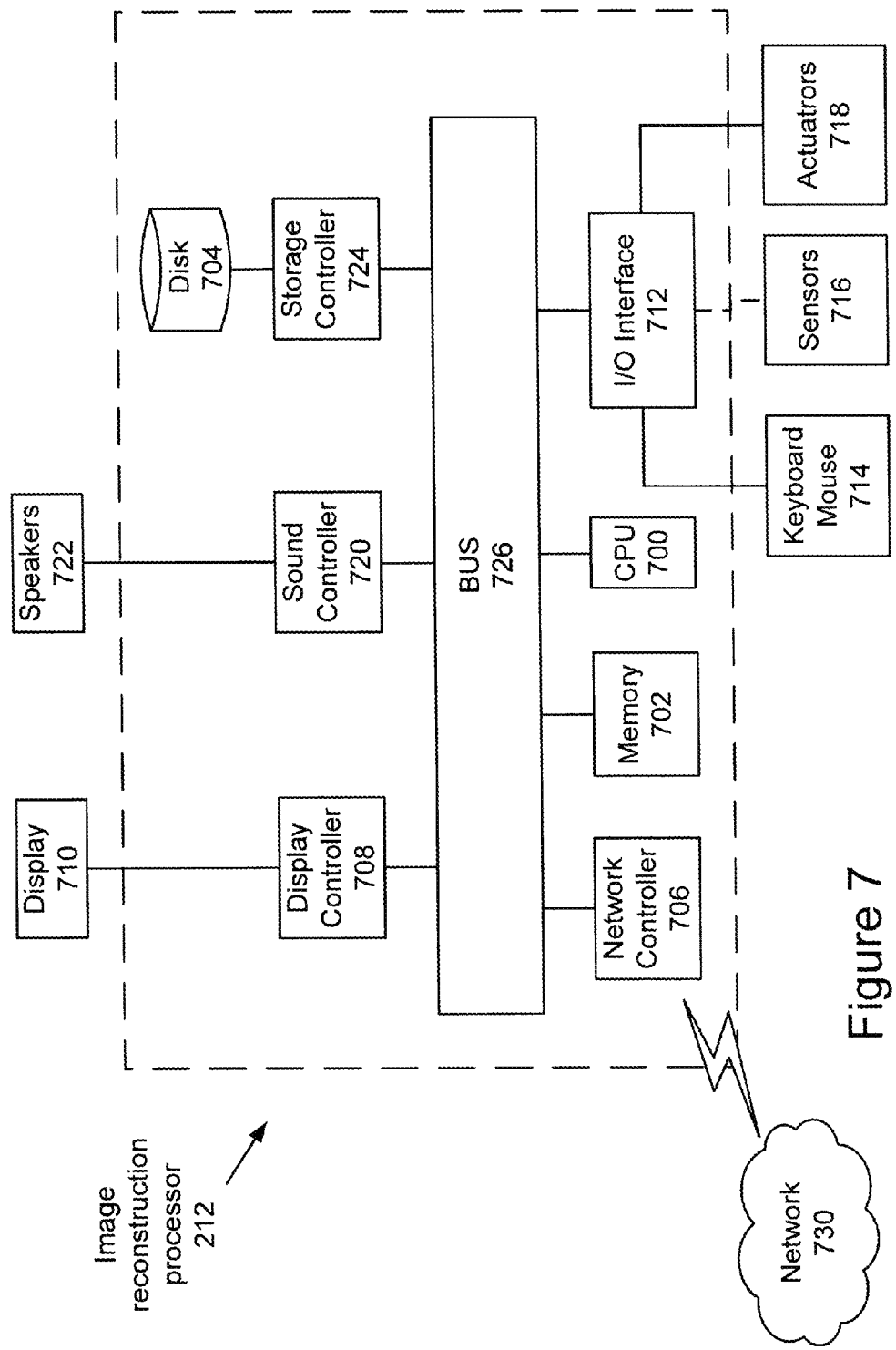
FIG. 7 shows a schematic diagram of an implementation of a image reconstruction processing unit.

FIG. 7 shows an implementation of the image reconstruction processor 212 that performs the method 400. Next, a hardware description of the image reconstruction processor 212 according to exemplary embodiments is described with reference to FIG. 7. In FIG. 7, the image reconstruction processor 212 includes a CPU 700 which performs the processes described herein. Process data and instructions may be stored in memory 702. Processes and instructions may also be stored on a storage medium disk 704 such as a hard drive (HDD) or portable storage medium or may be stored remotely. Further, this disclosure is not limited by the form of the computer-readable media on which the instructions are stored. For example, the instructions may be stored on CDs, DVDs, in FLASH memory, RAM, ROM, PROM, EPROM, EEPROM, hard disk or any other information processing device with which the image reconstruction processor 212 communicates, such as a server or computer.

Further, aspects of this disclosure may be provided as a utility application, background daemon, or component of an operating system, or combination thereof, executing in conjunction with CPU 700 and an operating system such as Microsoft Windows 7, UNIX, Solaris, LINUX, Apple MAC-OS and other systems known to those skilled in the art.

CPU 700 may be a Xenon or Core processor from Intel of America or an Opteron processor from AMD of America, or may be other processor types that would be recognized by one of ordinary skill in the art, such as an ARM-based processor. Alternatively, the CPU 700 may be implemented on an FPGA, ASIC, PLD or using discrete logic circuits, as one of ordinary skill in the art would recognize. Further, CPU 700 may be implemented as multiple processors cooperatively working in parallel to perform the instructions of the inventive processes described above.

The image reconstruction processor 212 in FIG. 7 also includes a network controller 706, such as an Intel Ethernet PRO network interface card from Intel Corporation of America, for interfacing with network 730. As can be appreciated, the network 730 can be a public network, such as the Internet, or a private network such as an LAN or WAN network, or any combination thereof and can also include PSTN or ISDN sub-networks. The network 730 can also be wired, such as an Ethernet network, or can be wireless such as a cellular network including EDGE, 3 G and 4 G wireless cellular systems. The wireless network can also be WiFi, Bluetooth, or another wireless form of communication.

The image reconstruction processor 212 further includes a display controller 708, such as a NVIDIA GeForce GTX or Quadro graphics adaptor from NVIDIA Corporation of America that respectively interface with a corresponding display 710, such as a Hewlett Packard HPL2445w LCD monitor.

The image reconstruction processor 212 further includes a general purpose I/O interface 712 interfaces with a keyboard and/or mouse 714 as well as sensors 716. The general purpose I/O interface 712 can also connect to a variety of actuators 718. The general purpose I/O interface 712 can also connect to a variety of peripherals including printers and scanners, such as an OfficeJet or DeskJet from Hewlett Packard.

A sound controller 720 is also provided in the image reconstruction processing unit 212, such as Sound Blaster X-Fi Titanium from Creative, to interface with speakers/microphone 722 thereby providing sounds and/or music.

The general purpose storage controller 724 connects the storage medium disk 704 with communication bus 726, which may be an ISA, EISA, VESA, PCI, or similar, for interconnecting all of the components of the image reconstruction processing unit 212. A description of the general features and functionality of the display 710, keyboard and/or mouse 714, as well as the display controller 708, storage controller 724, network controller 706, sound controller 720, and general purpose I/O interface 712 is omitted herein for brevity as these features are known.

While certain embodiments have been described, these embodiments have been presented by way of example only, and are not intended to limit the scope of the inventions. Indeed, the novel methods, apparatuses and systems described herein may be embodied in a variety of other forms; furthermore, various omissions, substitutions and changes in the form of the methods, apparatuses and systems described herein may be made without departing from the spirit of the inventions. The accompanying claims and their equivalents are intended to cover such forms or modifications as would fall within the scope and spirit of the inventions.

The invention claimed is:

1. An apparatus to reconstruct an image using combined third-generation energy-integrating computed tomography projection data and fourth-generation spectrally resolved computed tomography projection data, the apparatus comprising:
   processing circuitry configured to
      obtain first projection data from an energy-integrating detector;
      obtain second projection data from a photon-counting spectrally discriminating detector;
      perform a beam-hardening correction to the first projection data based on the second projection data; and
      reconstruct an image by solving a combined-system matrix equation formed by combining the corrected first projection data and the second projection data and using a combined-system matrix.

2. The apparatus according to claim 1, wherein the processing circuitry is further configured to:
   calculate a first basis image of a first material using the second projection data;
   calculate a second basis image of a second material using the second projection data; and
   correct the first projection data to remove effects of beam hardening by calculating a beam-hardening correction using the first basis image and the second basis image.

3. The apparatus according to claim 1, wherein the processing circuitry is further configured to:
   calculate a basis image using the second projection data; and
   correct the first projection data to remove effects of beam hardening by calculating a beam-hardening correction using the basis image.

4. The apparatus according to claim 2, wherein the processing circuitry is further configured to solve the combined-system matrix equation by an iterative computed tomography image reconstruction method.

5. The apparatus according to claim 2, wherein the processing circuitry is further configured to solve the combined-system matrix equation by calculating a pseudoinverse matrix of a combined-system matrix.

6. The apparatus according to claim 1, wherein the processing circuitry is further configured to:
   correct the first projection data to remove effects of beam hardening by calculating a beam-hardening correction using at least one basis image calculated by using the second projection data.

7. A computed tomography apparatus, comprising:
   a polychromatic X-ray source;
   an energy-integrating X-ray detector configured to generate first projection data;
   a photon-counting X-ray detector configured to generate second projection data; and
   processing circuitry configured to
      perform a beam-hardening correction to the first projection data based on the second projection data; and
      reconstruct an image by solving a combined-system matrix equation formed by combining the corrected first projection data and the second projection data and using a combined-system matrix.

8. The apparatus according to claim 7, wherein the processing circuitry is further configured to
   calculate a first basis image of a first material using the second projection data;
   calculate a second basis image of a second material using the second projection data; and
   correct the first projection data to remove effects of beam hardening by calculating a beam-hardening correction using the first basis image and the second basis image.

9. The apparatus according to claim 7, wherein the processing circuitry is further configured to
   calculate a basis image using the second projection data; and
   correct the first projection data to remove effects of beam hardening by calculating a beam-hardening correction using the basis image.

10. The apparatus according to claim 8, wherein the processing circuitry is further configured to solve the combined-system matrix equation by calculating a weighted pseudoinverse matrix of the combined-system system matrix.

11. The apparatus according to claim 8, wherein the processing circuitry is further configured to solve the combined-system matrix equation by an iterative computed tomography image reconstruction method.

12. The apparatus according to claim 8, wherein the processing circuitry is further configured to solve the combined-system matrix equation by calculating a pseudoinverse matrix of the combined-system matrix.

13. A method of image reconstruction using combined third-generation energy-integrating computed tomography projection data and fourth-generation spectrally resolved computed tomography projection data, the method comprising:
   obtaining first projection data from an energy-integrating detector;
   obtaining second projection data from a photon-counting spectrum-resolving detector;
   performing a beam-hardening correction to the first projection data based on the second projection data; and
   reconstructing an image by solving a combined-system matrix equation formed by combining the corrected first projection data and the second projection data and using a combined-system matrix.

14. The method according to claim 13, further comprising:
calculating a first basis image of a first material using the second projection data;
calculating a second basis image of a second material using the second projection data; and
correcting first projection data to remove effects of beam hardening by calculating a beam-hardening correction using the first basis image and the second basis image.

15. The method according to claim 14, wherein the reconstruction step comprises solving the combined-system matrix equation by calculating a pseudoinverse matrix of the combined-system system matrix.

16. The method according to claim 14, wherein the reconstruction step comprises solving the combined-system matrix equation by calculating a weighted pseudoinverse matrix of the combined-system system matrix.

17. The method according to claim 14, wherein the reconstruction step comprises solving the combined-system matrix equation by an iterative computed tomography image reconstruction method.

18. The method according to claim 14, wherein the reconstruction step comprises solving the combined-system matrix equation by a total-variation-minimization iterative computed tomography image reconstruction method.

19. The method according to claim 14, wherein the reconstruction step comprises solving the combined-system matrix equation by a Kamara iterative computed tomography image reconstruction method.

20. The method according to claim 14, further comprising:
respectively setting the first basis image and the second basis image equal to the corresponding first combined-system basis image and second combined-system basis image;
correcting the first projection data to remove the effects of beam hardening by calculating another beam-hardening correction using the first basis image and the second basis image; and
reconstructing another first combined-system basis image and another second combined-system basis image by solving the combined-system matrix equation using the corrected first projection data and the second projection data.

* * * * *